United States Patent [19]

Glassman

[11] Patent Number: 4,579,554
[45] Date of Patent: Apr. 1, 1986

[54] INDWELLING URINARY CATHETER

[76] Inventor: Jacob A. Glassman, 1680 Michigan Ave., Miami Beach, Fla. 33139

[21] Appl. No.: 575,034

[22] Filed: Jan. 30, 1984

[51] Int. Cl.$^4$ ............................................. A61M 29/00
[52] U.S. Cl. ....................................... 604/102; 604/96
[58] Field of Search ..................................... 604/43–45, 604/102, 105, 96

[56] References Cited

U.S. PATENT DOCUMENTS

| | | | |
|---|---|---|---|
| 2,257,369 | 9/1941 | Davis | 604/43 |
| 3,394,705 | 7/1968 | Abramson | 604/43 |
| 3,815,608 | 6/1974 | Spinosa | 604/105 |
| 3,821,956 | 7/1974 | Gordhamer | 604/264 |
| 4,445,897 | 5/1984 | Ekbladh et al. | 604/43 |
| 4,501,580 | 2/1985 | Glassman | 604/102 |

FOREIGN PATENT DOCUMENTS 2240026  3/1975  France .

Primary Examiner—C. Fred Rosenbaum
Assistant Examiner—Gene B. Kartchner
Attorney, Agent, or Firm—Elmer L. Zwickel

[57] ABSTRACT

An indwelling urinary catheter that includes a novel arrangement whereby the entire outside penile urethral portion of the catheter tube and substantially the entire length of the surrounding mucos of the penile urethral canal may be periodically irrigated and cleansed of waste, bacterial debris, etc, without periodic withdrawal and cleaning of the catheter form the urethral canal. Means are provided also to facilitate distribution of medicinal jel into the lacuna navicularis area of the urethral canal and to protect the penile catheter junction in order to prevent urethral infection.

5 Claims, 7 Drawing Figures

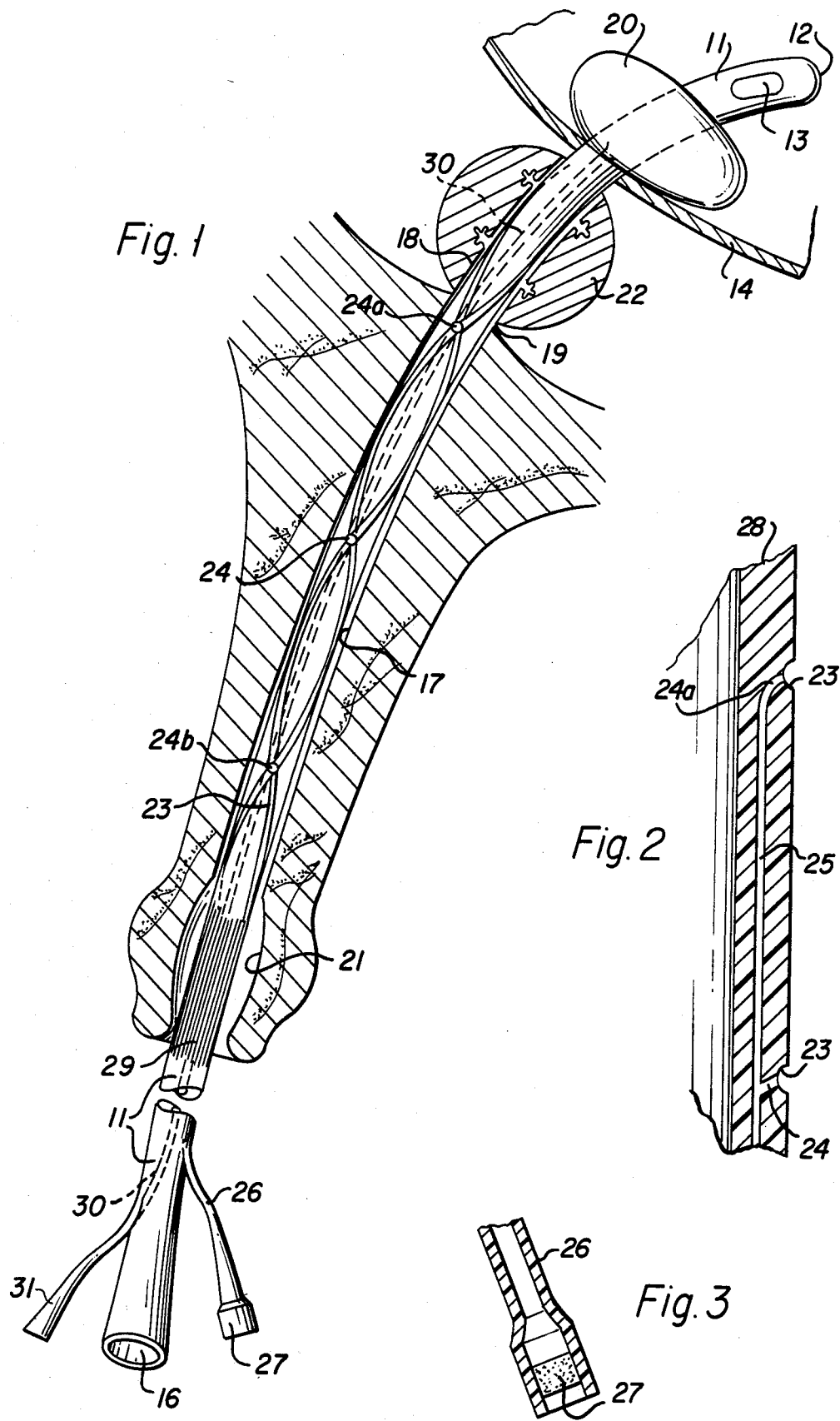

INDWELLING URINARY CATHETER

The present invention relates to improvements in indwelling urinary catheters of a type generally shown and described in my abandoned U.S. applications Ser. Nos. 161,920, and 326,664, respectively, filed June 23, 1980 and Dec. 3, 1981.

BACKGROUND OF THE INVENTION

Even though the herein disclosed catheter need never be withdrawn from the urethra for bacterial cleansing to eliminate bacterial contamination, a thorough flushing of the indwelling catheter and urethra with disinfectant solution is easily effected. Normally, all male patients having an indwelling catheter in their penis, and all female patients having an indwelling catheter in their urethra hardly ever receive a detailed catheter-toilette specifically directed toward the pari-catheter space between the urethral mucosa and the outside surface of the urethral portion of the catheter.

The main reason for such neglect is that there has not been any accepted effective method, technique or medical instrument capable of meeting this problem head on. The herein indwelling urinary catheter is specifically structured to meet this serious problem and still permit indwelling urinary drainage to continue uninterruptedly with absolute safety. Unavoidable leakage of bladder urine into the peri-catheter space is usually the result of uninhibited contractions of the detrusor muscle which is so often seen in patients with neurological diseases, or because of the catheter riding up to lift it's balloon off the bladder floor. For those who have a neurological problem, an indwelling catheter of the well known FOLEY type must presently be changed very often to avoid the development of encrustations, concretions (stones), and gram-negative bacterial infection with sepsis.

Before entering into a detailed discussion of the present catheter and it's use, it should be worth the effort to review some of the problems often arising in the use of the known type of catheters. All catheters previously designed to irrigate the penile urethra and provided with orifices situated at the base of the bladder are doomed to failure: First; the prostate gland is almost always hypertrophied and invariably the prostatic uretheral canal is so constricted that catheterization is required. To insert a catheter having perforations that rest within the prostate canal is to obviate the possibility of an irrigating fluid from escaping from the perforations into the prostatic canal. Second, a catheter often rides up into the bladder for about 1 to 4 inches and those catheters with perforations below the bladder-empty their fluids into the infected bladder instead of into the sterile penile urethra. Instead of being able to prophylactically prevent urethral infection, the catheter with sub-bladder perforations actually leaks contaminated bladder urine into the urethra around the catheter and contaminates the urethra.

Further, catheterization is reserved for those patients with prostatic canal constriction and occlusion and in whom normal urination is difficult or impossible. Catheters designed for urethral irrigations that have their outlet openings below the bladder neck cannot possibly function between the tight fitting around the catheter blocks the irrigation solution from entering into the prostatic urethral canal. The McKay patent of record, specifically teaches a catheter that overcomes the tight circumferential constriction of the prostatic urethral canal about the catheter wall, only because McKay creates and maintains sufficient fluid pressure to specifically overcome the prostatic tightness around the catheter.

The herein disclosed catheter embodies characteristics of the catheter disclosed in the aforesaid applications, except that, in this disclosure, the specific fluid openings are spaced along the length of the catheter tube and are associated with a deep spiral channel or channels that enables the fluid to flow on the catheter tube surface upwardly toward the bladder neck and downwardly along the penile urethra toward the lacuna navicularis and glans penis.

Only because of the free flow of irrigating or antibiotic solutions along the deep spiral channel, the cleansing action is able to encompass the areas of the membranous urethra and prostatic urethra, both of which have heretofore been omitted from the benefits of urethral irrigation. Further, should the catheter work it's way upwardly in a direction to carry the tube and balloon high up into the bladder, the instant catheter prevents the entrance of the antiseptic solution into the bladder.

The instant catheter tube also includes a multitude of circumferentially spaced, axially aligned, deep-cut grooves on the outside of the catheter surface adjacent to it's proximate end which are useful to retain an antiseptic ointment or jel to prevent infection of the lacuna navicularis as well as to retard an ascending infection that starts out at the penile-catheter junction. These grooves are in flow communication with the deep spiral channels.

ADVANTAGES OF THE INVENTION

The improved catheter is the only known catheter that meets all the necessary and acceptable requirements for an effective and safe indwelling catheter; the qualifications and advantages of which may be stated as follows:

1. The urinary bladder is allowed to drain effectively and the urinary flow can be accurately measured at any period of time, especially by micro-meter collectors;
2. The infected urinary bladder (cystitis) may be irrigated with sterile saline or antiseptic or anti-biotic solutions without any problem. No intermixing of sterile and non-sterile fluids is possible;
3. The novel structure allows for irrigation of the prostatic and the membranous urethra through the free flow of disinfecting solution along the deep-cut channels on the outside surface on the outside surface of the catheter, even though the prostatic canal may have become constricted to firmly embrace and obstruct the catheter openings within the prostatic canal;
4. Prevent peri-catheter stagnation and obstruction of the mucosal glandular secretions of the urethra. Perfect unobstructed peri-catheter irrigation and drainage prevents encrustations, concretion formation and subsequent gram-negative bacterial infection and ultimately a serious and possible systemic infection with ultimate generalized sepsis;
5. Elimination of the need for repeated indwelling catheterization which so often predisposes to serious infection because of the failure to perform so-called "strict-toilette" which in reality means the lack of strictly sterile precautions and questionable management of follow-up serious catheterization, There is often a let-down of the required strict aseptic technics that are mandatory during catheterization; and in the absence of the necessary sterile or clean surroundings' repeated indwelling catheterization will invariably predispose to the serious hazard, a discomfort, health risk, and even life itself.

The present disclosure, having it's fluid distribution means (perforation) critically terminating below the prostatic urethra canal will not have fluid flow hampered by enlargement and tightness of the prostate, or by movement of the catheter inwardly toward the bladder. The reason being that there are no perforations immediatly below the bladder neck or within the prostatic canal. However, the deep-cut channels continue to extend upwardly toward the base of the bladder.

Various features of novelty which characterize the invention are pointed out particularly in the claims appended and forming part of this disclosure. For better understanding of the invention, it's operation, advantages and specific objects attained by it's use, reference made to the accompanying drawings and descriptive matter of the invention.

FIG. 1 is a schematic illustration of the male urethra tract, illustrating the detail structural characteristics of the improved indwelling catheter;

FIG. 2 is an enlarged fragmentary longitudinal sectional view of the wall of the catheter, along the line of perforations and showing the flow communication between the perforations and the deep grooves;

FIG. 3 is a detail sectional view of the external extension of the catheter tube, showing the penetratable block therein;

Figure 4:
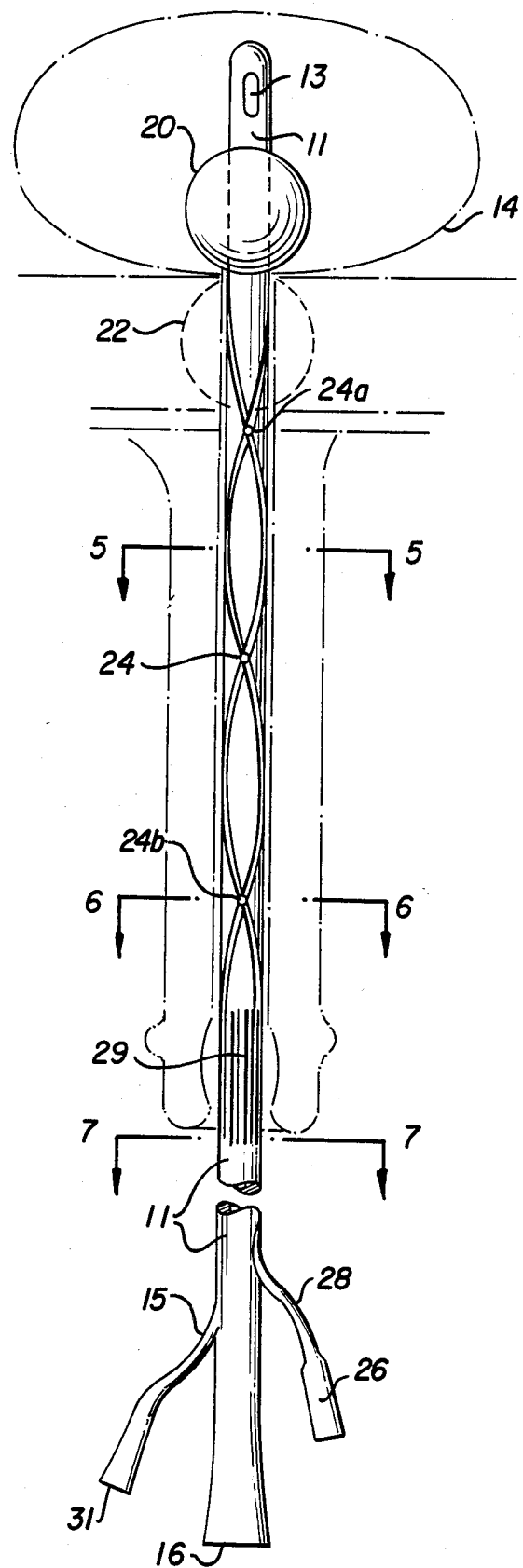
Figure 5:
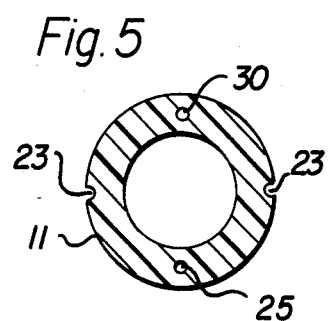
Figure 6:
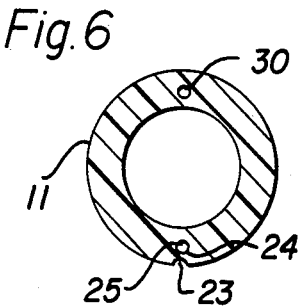
Figure 7:
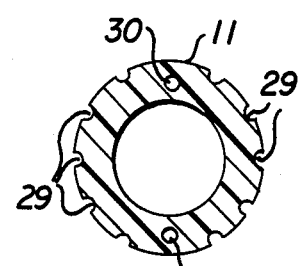

FIG. 4 is an elevational view of the catheter showing the relationship with the penile canal; and FIGS. 5, 6 and 7 are each a transverse sectional view of the catheter, viewed along lines 5—5, 6—6; and 7—7 of FIG. 4.

DESCRIPTION OF STRUCTURE

Referring to the embodiment of the improved indwelling catheter illustrated in FIGS. 1-7, and particularly to FIG. 1, the catheter comprises a small diameter tube 11, having a length of approximately 34-44 cms., formed of resilient material, such as silicone compound or other non-toxic substance, including latex and/or rubber. The catheter tube 11, which is basically similar to the well known FOLEY indwelling catheter, has a closed insert or distal end 12 and flow aperture 13 inwardly of said end which is to be located within the bladder 14. The distal end 12 carries a balloon 20 which when inflated by entrance of pressurized fluid delivered to the balloon through a wall passage 30 that opens to atmosphere at the proximate end of the tube, as at 31. The proximate end of the tube, is open and is adapted to have it's outlet 16 connected in flow communication with a drain (not shown) for conveying fluid from the bladder to a receptacle for disposal.

In order to negate the many dangers of urinary drainage down along the outside of the catheter tube 11, the improved catheter embodies novel means to wash and cleanse the outside surface of the catheter and the mucosa of the penile urethra canal 17 and indirectly irrigate the prostatic urethra 18 and the membraneous urethra 19. In the FIG. 1 embodiment the outside surface of the catheter tube, starting adjacent the lacuna navicularis 21 and extending to approximately the base of the bladder area, is provided with a deep cut groove or grooves 23 that preferably are arranged spirally around the tube. All the deep cut grooves connect substantially midway the longitudinal center of the catheter with flow openings 24 that are in flow communication with a passage 25 (FIG. 2) in the catheter wall 28. This passage terminates in an external extension 26 having a penetrable block 27 (FIG. 3) at it's end to admit a sterile needle required to inject sterile irrigating fluid into the passage 25 for delivery to the deep cut grooves 23. The deep cut groove or grooves, extending in both directions from the center passage flow opening 24, may have additional flow openings 24a and 24b in communication therewith. Thus, the flow passages 23-24 carry sterile antiseptic or antibiotic fluid to the groove or grooves wherein it flows in the direction of the prostate gland 22 and bladder 14.

It should be noted at this time, that even though the prostatic urethra 18 may be constricted, as is commonly the case in patients of advanced age, the sterile antiseptic fluid can still enter the prostatic urethra and flow and distribute itself over the surface of the catheter tube 11, by reason of the deep cut grooves 23 and thus effectively irrigate the constricted prostatic urethra 18 and delicate membranous urethra 19 that no catheter having perforations only and no flow grooves can possibly accomplish.

The indwelling catheter 11 also includes novel means to irrigate and medicate the lacuna narvicularis 21 and the adjacent penile-catheter junction at the proximate end of the urethral canal. As best shown in FIGS. 1, 4 and 7, this means may take the form of a multitude of short circumferentially spaced parallel deep cut grooves 29 (approximately 3 to 5 cms. in length) on the outside surface of the catheter. These parallel longitudinal cut-out grooves are so located that they extend upwardly beyond the area of the lacuna naviculalris 21 and downwardly to beyond and outside of the penis. Thus a medicament jel can be applied to the exposed portions of the deep cut longitudinal grooves which, upon the softening of the jel, will carry the jel upwardly into the lacuna navicularis 21 where it will act upon the bacterial infections which originate and incubate therein. Such upward movement of the jel is assisted by having the proximate end of the spiral channels terminate in the parallel grooves.

It should be apparent that the urethral catheter disclosed affords novel means to irrigate not only the main penile urethra, but also effectively admit antiseptic fluid and antibiotics into the prostatic urethra and membraneous urethra, irrespective of whether or not these urethral areas have become constricted or obstructed. The primary reason for this is because the fluid flowing along and beyond the deep cut grooves 23 enters the constricted prostate urethra unrestrained by the extreme snugness of the surrounding prostatic urethra and difficulty in distributing itself within the canal. Also, the presence of the deep-cut channel 23 on the catheter's exterior below the bladder insures distribution of sterile irrigating fluid throughout the length of the penile urethra, and not just in the prostatic area as has been the case with McKay's type of catheter.

While a specific embodiment of the invention has been shown and described in detail to illustrate the application of the invention and it's principles, it will be understood that the invention may be embodied in other manners without departing from the principles herein disclosed.

I claim:

1. A urethral catheter comprising:
   a. an elongated member including a tubular wall having inner and outer surfaces,
   b. said elongated member being open at its distal end and at its proximal (proximate) end;
   c. said inner surface extending the length of (the) said elongated member and defining an unbroken flow duct to receive fluids from a bladder and convey them to said proximal (the proximate) end for discharge;
   d. at least one relatively deep channel (groove) on said (the) outer surface of said (the) tubular wall extending from near said proximal (the proximate) end of said (the) tubular wall to a distance short of said (the) distal end (;and),
   e. a fluid passageway in said tubular wall; said passageway having an ixternal flow communication with a source of fluid and at least one opening connecting said passageway with (the) said channel (groove) for distribution onto (the) said outer surface; and
   f. a multitude of parallel circumferentially spaced deep cut-out grooves in the exterior surface of said tubular member, said grooves beginning at the distal end of said channel and extending proximally along said tubular member.

2. The urethral catheter recited in claim 1, (wherein) further comprising an inflatable balloon mounted on and located near the distal end of (the tube) said tubular member, whereby when the catheter is placed in the bladder, the inflated balloon will (seats) seat snugly against the bladder floor to resist excape of infected fluids into the sterilely treated urethra.

3. The urethral catheter recited in claim 1, wherein (the) said deep channel is (grooves are) arranged spirally around (the tube) said tubular member.

4. A catheter for irrigating a bladder comprising:
   a. a resilient tube of a size to loosely fit within and extend through the penile urethra and into the bladder,
   b. at least one deep cut-out (groove) channel extending longitudinally on the exterior surface of said tube terminating short of the lacuna navicularis to effect distribution of antiseptic fluid over a major portion of the outside surface of said tube and over substantially the entire surface and length of the urethral and prostate canals,
   c. a fluid passageway in the wall of said tube for delivering fluid to said (groove) channel,
   d. and a multitude of parallel circumferentially spaced deep cut-out grooves on the exterior surface of said tube coincidental with the tube axis, said grooves being arranged on said tube below the terminus of, and flow connected to, the distal end of said channels.

5. The urethral catheter recited in claim 1, wherein said channel is in fluid communication with said grooves.

* * * * *